(12) United States Patent
Byrum et al.

(10) Patent No.: US 7,500,944 B2
(45) Date of Patent: Mar. 10, 2009

(54) IMPLANTABLE BAND WITH ATTACHMENT MECHANISM

(75) Inventors: Randal T. Byrum, South Lebanon, OH (US); Kristin L. Jambor, Cincinnati, OH (US); Sean P. Conlon, Loveland, OH (US); Norman Crawford, Washington Courthouse, OH (US); Kevin A. Harper, Mason, OH (US); Lawrence Spreckelmeier, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 453 days.

(21) Appl. No.: 10/741,869

(22) Filed: Dec. 19, 2003

(65) Prior Publication Data

US 2004/0267293 A1 Dec. 30, 2004

Related U.S. Application Data

(60) Provisional application No. 60/507,916, filed on Sep. 30, 2003, provisional application No. 60/483,353, filed on Jun. 27, 2003.

(51) Int. Cl.
*A61F 2/00* (2006.01)
(52) U.S. Cl. ...................................................... 600/37
(58) Field of Classification Search ............... 24/16 PB; 128/876, 897–899; 424/423; 63/3.1, 25; 600/16, 29–32, 37, 40, 593; 601/153; 606/53, 606/151–158; 623/3.1
See application file for complete search history.

(56) References Cited

U.S. PATENT DOCUMENTS

| | | | |
|---|---|---|---|
| 2,637,887 A | 5/1953 | Goodman et al. | |
| 3,080,635 A | 3/1963 | Gunther et al. | |
| 3,214,808 A * | 11/1965 | Litwin | 24/16 BP |
| 3,576,054 A | 4/1971 | Rynk | |
| 3,605,726 A * | 9/1971 | Williams et al. | 600/504 |
| 3,726,279 A * | 4/1973 | Barefoot et al. | 606/151 |
| 3,860,997 A | 1/1975 | Van Riper, Jr., et al. | |
| 4,037,603 A | 7/1977 | Wendorff | |
| 4,154,418 A * | 5/1979 | Wiese | 248/316.1 |
| 4,458,395 A | 7/1984 | Aoki | |
| 4,478,219 A | 10/1984 | Rozario et al. | |
| 4,532,868 A | 8/1985 | Gleichaut et al. | |
| 4,538,304 A * | 9/1985 | Grafelmann | 433/176 |

(Continued)

FOREIGN PATENT DOCUMENTS

EP 0 611 561 A1 9/1993

(Continued)

OTHER PUBLICATIONS

EPO Search Report dated Jan. 18, 2005 for related European Patent Application No. EP 04 25 6021.

(Continued)

Primary Examiner—Samuel G Gilbert
(74) Attorney, Agent, or Firm—Dean Garner (57) ABSTRACT

An implantable band for placement around an anatomical passageway, such as the stomach or other lumen, has the inner surfaces at each end attached to each other in the operative position. One end may include a passageway through which the other end extends. A lateral member may extend from the surface at one end and engage the other end.

18 Claims, 6 Drawing Sheets

U.S. PATENT DOCUMENTS

| | | | |
|---|---|---|---|
| 4,592,339 A | 6/1986 | Kuzmak et al. | |
| 4,592,355 A | 6/1986 | Antebi | |
| 4,688,337 A | 8/1987 | Dillner et al. | |
| 4,706,914 A | 11/1987 | Ground | |
| 4,779,314 A | 10/1988 | Aoki | |
| 4,854,014 A | 8/1989 | Ueno | |
| 4,907,513 A | 3/1990 | Manion et al. | |
| 5,028,027 A | 7/1991 | Fraser | |
| D319,311 S * | 8/1991 | Kohler | D24/143 |
| 5,074,868 A | 12/1991 | Kuzmak | |
| 5,152,770 A | 10/1992 | Bengmark et al. | |
| 5,160,338 A | 11/1992 | Vincent | |
| 5,226,429 A | 7/1993 | Kuzmak | |
| 5,249,338 A | 10/1993 | Aoki | |
| 5,274,889 A | 1/1994 | Morita | |
| 5,363,536 A | 11/1994 | Kleeman | |
| 5,449,368 A | 9/1995 | Kuzmak | |
| 5,527,355 A | 6/1996 | Ahn | |
| 5,584,452 A * | 12/1996 | Koike | 248/74.3 |
| 5,601,604 A * | 2/1997 | Vincent | 606/216 |
| 5,604,604 A | 2/1997 | Fan | |
| 5,683,404 A | 11/1997 | Johnson | |
| 5,707,378 A | 1/1998 | Ahn et al. | |
| 5,843,170 A * | 12/1998 | Ahn | 623/1.34 |
| 5,843,179 A | 12/1998 | Vanney et al. | |
| 5,868,140 A * | 2/1999 | Miller et al. | 128/898 |
| 6,461,292 B1 | 10/2002 | Forsell | |
| 6,470,892 B1 | 10/2002 | Forsell | |
| 6,511,490 B2 | 1/2003 | Robert | |
| 6,782,572 B1 | 8/2004 | Jones | |
| 2002/0087431 A1 | 7/2002 | Morishima | |
| 2002/0183768 A1* | 12/2002 | Deem et al. | 606/151 |
| 2002/0198548 A1 | 12/2002 | Robert | |
| 2003/0105385 A1 | 6/2003 | Forsell | |
| 2003/0114729 A1 | 6/2003 | Forsell | |
| 2004/0230137 A1* | 11/2004 | Mouton | 600/593 |
| 2004/0267291 A1 | 12/2004 | Byrum et al. | |
| 2004/0267292 A1 | 12/2004 | Byrum et al. | |
| 2005/0125014 A1* | 6/2005 | Duluco et al. | 606/151 |

FOREIGN PATENT DOCUMENTS

| | | |
|---|---|---|
| EP | 0 611 561 B1 | 9/1993 |
| EP | 0 702 529 B1 | 5/1994 |
| EP | 1 205 148 A1 | 5/1994 |
| EP | 608580 | 8/1994 |
| EP | 0 885 031 B1 | 6/1997 |
| EP | 0 923 356 B1 | 6/1998 |
| EP | 1 091 707 A1 | 6/1999 |
| EP | 1 036 545 A2 | 3/2000 |
| EP | 1 113 767 A0 | 3/2000 |
| EP | 1 198 211 A1 | 7/2000 |
| EP | 1 216 012 A1 | 9/2000 |
| EP | 1 237 486 A2 | 12/2000 |
| EP | 1 244 399 A 1 | 12/2000 |
| EP | 1 251 808 A1 | 1/2001 |
| EP | 1 259 170 A2 | 3/2001 |
| EP | 1281360 | 7/2002 |
| FR | 2 825 264 | 12/2002 |
| FR | 2 825 264 A | 12/2002 |
| FR | 2 827 756 | 1/2003 |
| FR | 2 827 756 A | 1/2003 |
| GB | 2 139 902 A | 5/1984 |
| JP | 08052147 | 8/1994 |
| JP | 09117454 A | 10/1995 |
| WO | WO 86/04498 | 8/1986 |
| WO | WO 87/00034 | 1/1987 |
| WO | WO 92/02182 | 2/1992 |
| WO | WO 92/21293 | 12/1992 |
| WO | WO 94/05214 | 3/1994 |
| WO | WO 94/27504 | 12/1994 |
| WO | WO 98/56321 | 12/1998 |
| WO | WO 99/34748 | 7/1999 |
| WO | WO 99/34748 A | 7/1999 |
| WO | WO 00/69376 | 11/2000 |
| WO | WO 01/10359 A1 | 2/2001 |
| WO | WO 01/19297 A1 | 3/2001 |
| WO | WO 01/24742 A1 | 4/2001 |
| WO | WO 01/41671 A2 | 6/2001 |
| WO | WO 01/45597 A1 | 6/2001 |
| WO | WO 01/52777 | 7/2001 |
| WO | WO 01/68007 A1 | 9/2001 |
| WO | WO 01/85071 A1 | 11/2001 |
| WO | WO 02/053040 A1 | 7/2002 |
| WO | WO 02/064041 A1 | 8/2002 |
| WO | WO 02/071951 A1 | 9/2002 |
| WO | WO 02/091961 A1 | 11/2002 |
| WO | WO 02/096326 A2 | 12/2002 |
| WO | WO 02/096327 A2 | 12/2002 |
| WO | WO 03/101352 | 12/2003 |

OTHER PUBLICATIONS

Office Action dated Dec. 15, 2004 for U.S. Appl. No. 10/677,088, filed Sep. 30, 2003.
Amendment and Response dated Mar. 11, 2005 for U.S. Appl. No. 10/677,088, filed Sep. 30, 2003.
Office Action dated Oct. 19, 2004 for U.S. Appl. No. 10/676,368, filed Sep. 30, 2003.
Amendment and Response dated Feb. 18, 2005 for U.S. Appl. No. 10/676,368, filed Sep. 30, 2003.
Office Action dated May 11, 2005 for U.S. Appl. No. 10/676,368, filed Sep. 30, 2003.
US Patent Office Action dated Aug. 25, 2005, for U.S. Appl. No. 10/677,088, filed Sep. 30, 2003.
Amendment and Response to Office Action filed on Dec. 20, 2005 for U.S. Appl. No. 10/677,088, filed Sep. 30, 2003.
Amendment dated Feb. 18, 2005 U.S. Appl. No. 10/676,368.
Notice of Allowance dated Sep. 25, 2007 for U.S. Appl. No. 10/677,088.
Office Action dated May 8, 2007 for U.S. Appl. No. 10/677,088.
Office Action dated Sep. 21, 2005 for U.S. Appl. No. 10/676,368.
Indian Search Report, Serial No. 357/KOL/2004, p. 1.
U.S. Appl. No. 60/507,612, filed Sep. 30, 2003, Byrum et al.
U.S. Appl. No. 60/507,625, filed Sep. 30, 2003, Byrum et al.
U.S. Appl. No. 10/676,368, filed Sep. 30, 2003, Byrum et al.
U.S. Appl. No. 10/742,483, filed Dec. 19, 2003, Byrum et al.
EPO Communication dated Sep. 24, 2004 for Application No. EP 04256037.
EPO Search Report dated Mar. 23, 2005 for EPO 04 25 6037.5.
Notice of Allowance dated Sep. 26, 2007 for Application Serial No. 10/742,483.
Office Action dated Apr. 6, 2007 for Application Serial No. 10/742,483.
Office Action dated Jun. 11, 2008 for Application Serial No. 10/874,881.

* cited by examiner

IMPLANTABLE BAND WITH ATTACHMENT MECHANISM

RELATED APPLICATIONS

This application claims priority from U.S. Provisional Patent Application Ser. No. 60/483,353, titled Adjustable Gastric Band Having An Improved Attachment Mechanism, filed on Jun. 27, 2003, and U.S. Provisional Patent Application Ser. No. 60/507,916, titled Implantable Band With Attachment Mechanism, filed on Sep. 30, 2003, the disclosures of both of which are incorporated herein by reference. This application also incorporates by reference co-pending United States Patent Application filed of even date herewith, application Ser. No. 10/742,483, pending titled Implantable Band Having Improved Attachment Mechanism, inventors Byrum, Jambor and Albrecht. This application also incorporates by reference the following co-pending United States Patent Applications filed on Sep. 30, 2003: application Ser. No. 10/677,088, pending titled Implantable Band with Transverse Attachment Mechanism, inventors: Byrum, Jambor and Crawford; application Ser. No. 10/676,368, abandoned titled Implantable Band with Non-Mechanical Attachment Mechanism, inventors: Byrum and Nuchols; Provisional Application Ser. No. 60/507,625, Implantable Band Having Improved Attachment Mechanism, inventors: Byrum, Jambor and Albrecht; and Provisional Application Ser. No. 60/507,916, Implantable Band with Deformable Attachment Mechanism, inventors: Byrum, Wiley, Conlon and Fender.

TECHNICAL FIELD

This present invention relates generally to a surgically implantable band for encircling an anatomical passageway, and is particularly directed to an adjustable gastric band for encircling the stomach for the control of obesity. The invention will be specifically disclosed in connection with an improved attachment mechanism for an adjustable gastric band.

BACKGROUND OF THE INVENTION

Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that is less than the normal interior diameter of the stomach that restricts food passing from an upper portion to a lower digestive portion of the stomach. When the stoma is of the appropriate size, food held in the upper portion of the stomach provides a feeling of fullness that discourages overeating.

In addition to a latched position to set the diameter of the gastric band, adjustability of gastric bands is generally achieved with an inwardly directed inflatable balloon, similar to a blood pressure cuff, into which fluid, such as saline, is injected through a fluid injection port to achieve a desired diameter. The balloon is typically deflated or only partially inflated when first placed in the body to allow for body adjustments and healing around the new band site. Since adjustable gastric bands may remain in the patient for long periods of time, the fluid injection port is typically installed subcutaneously to avoid infection, for instance in front of the sternum. Following the initial implantation, the surgeon may adjust the band by loosing or tightening depending on the patients' needs. Adjusting the amount of fluid in the adjustable gastric band is achieved by inserting a Huber tip needle through the skin into a silicone septum of the injection port. Once the needle is removed, the septum seals against the hole by virtue of compressive load generated by the septum. A flexible conduit communicates between the injection port and the adjustable gastric band.

An attachment mechanism for the adjustable gastric band has to provide an initial sizing of the stoma of the stomach. One generally known attachment is to suture ends of the adjustable gastric band. Another generally known attachment includes one end of the gastric band terminating in a flexible conduit that has a flared portion that is drawn through an opening in a second end of the gastric band and then sutured to the encircling band portion—securing the band to the stomach. After the sutures are in place, the injection port is anchored at a convenient location.

While these known approaches are effective in securing the gastric band, further improvements are desired that simplify the clinical implantation procedure, that provide long-term reliability, and that facilitate readjustment or removal.

While sutures have been relied on as the most positive connection in the past, it is desirable to have a secure attachment that does not require sutures, yet does not require a large force to create the secure attachment. Otherwise, it may be difficult to adequately grip and perform the attachment with laparoscopic instruments. Consequently, a significant need exists for an adjustable gastric band having an improvement attachment mechanism.

SUMMARY OF THE INVENTION

The present invention addresses these and other problems in the prior art, by providing an adjustable gastric band device that is engaged with less force, thereby facilitating implementation with laparoscopic instruments, yet the attachment remains secure over long term use.

A general object of this invention is to provide an adjustable gastric band having an opposing inner surface attachment mechanism.

Another object of this invention is to provide a readily reversible adjustable gastric band which can be fastened and unfastened without reducing the holding strength of the attachment mechanism.

Another object of this invention is to provide an adjustable gastric band having longitudinal forces that are transferred through the attachment mechanism that may be relatively large without causing detachment, while engagement forces are relatively low.

To achieve the foregoing and other objects, and in accordance with the purposes of the present invention as described herein, there are described adjustable gastric bands with opposing surface attachment mechanisms having a member extending laterally from one end which is configured to engage the other end. In accordance with one aspect, the lateral member includes a passageway which receives a portion of the other end. In another aspect, the lateral member is received by an opening in the other end.

Further novel features and other objects of the present invention will become apparent from the following detailed description, discussion and the appended claims, taken in conjunction with the drawings.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

Reference will now be made in detail to the present preferred embodiment of the invention, an example of which is illustrated in the accompanying drawings.

DETAILED DESCRIPTION OF EMBODIMENTS OF THE INVENTION

In the following description, like reference characters designate like or corresponding parts throughout the several views. Also, in the following description, it is to be understood that terms such as front, back, inside, outside, and the like are words of convenience and are not to be construed as limiting terms. Terminology used in this patent is not meant to be limiting insofar as devices described herein, or portions thereof, may be attached or utilized in other orientations. Referring in more detail to the drawings, the invention will now be described.

Figures 1, 2:
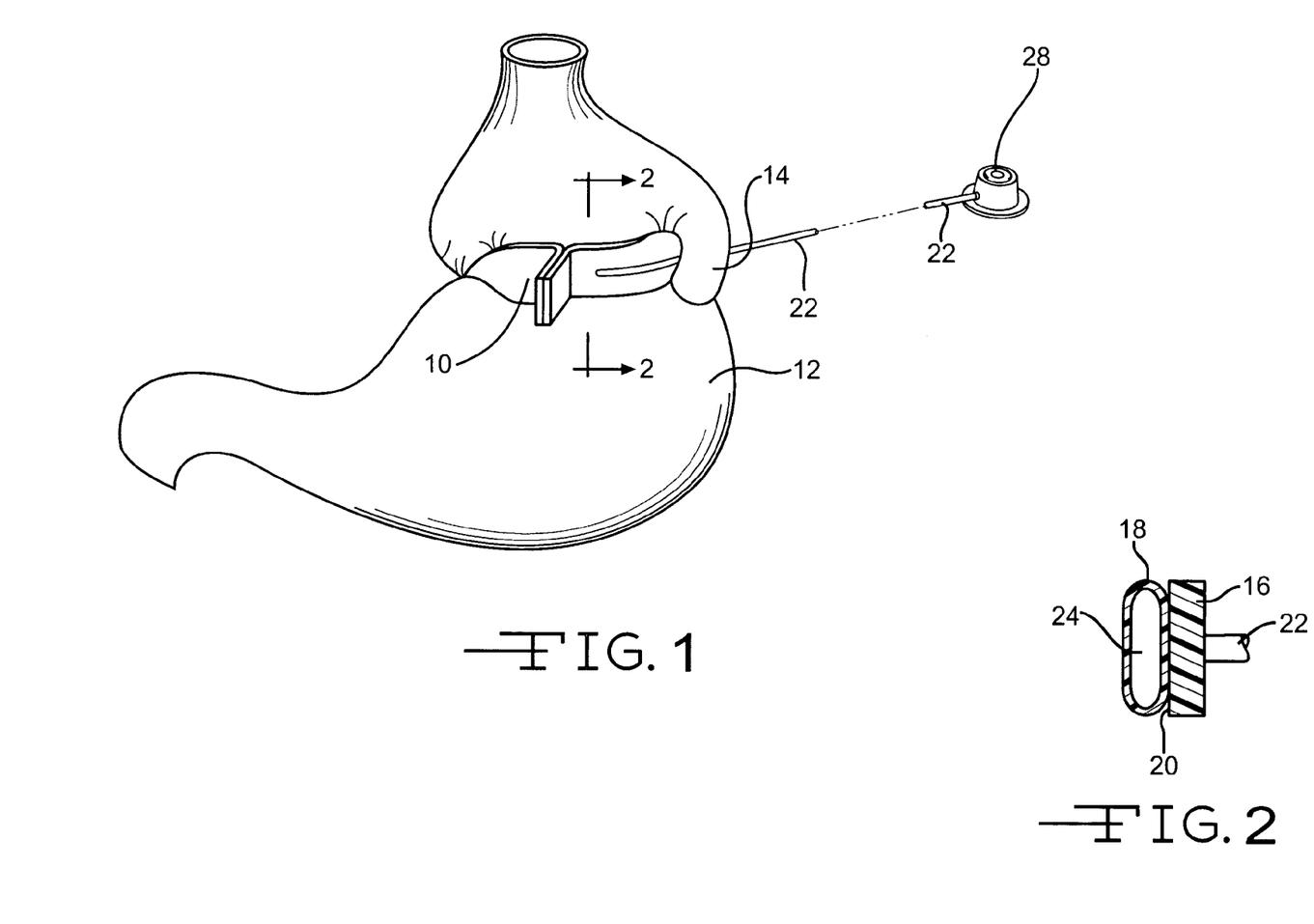
FIG. 1 is a diagrammatic drawing showing an adjustable gastric band wrapped around an upper part of a stomach.
FIG. 2 is a cross sectional view of the adjustable gastric band of FIG. 1 taken along line 2-2.

Referring to FIG. 1, an adjustable gastric band 10 is shown wrapped around an upper portion of a stomach 12, kept in place by attaching the two ends together and extending a portion 14 of the stomach 12 over the adjustable gastric band 10 by suturing portion 14 to the stomach. Referring also to FIG. 2, the adjustable gastric band 10 includes a non-extensible strap 16 and an inflatable balloon 18, made of a medical grade silicone polymer or any other suitable material, is carried by the inner surface 20 of the strap 16. The balloon 18 may be secured to the inner surface 20 in any well known manner, or even made of unitary construction with the strap 16, although the strap 16 may typically be formed of a different material.

One end of a flexible conduit 22 is in fluid communication with the internal cavity 24 of the balloon 18, with the other end being in fluid communication with an internal cavity (not shown) of a remote injection port 26. The remote injection port 26 includes a silicone septum 28. At the time the adjustable gastric band 10 is implanted around a portion of the stomach, the remote injection port 26 is also implanted at a suitable location, usually within the rectus sheaths, for transcutaneous access via a Huber needle.

As is well known, the internal cavity 24, the flexible conduit 22 and the internal cavity of the remote injection port 26 are preferably at least partially filled with a physiologically compatible fluid, such as a saline solution. Postoperative adjustment of the perimeter enclosed by the balloon 18, and therefore the size of the stoma, is accomplished by addition or removal of fluid from the interior cavity 24 of the balloon 18 by inserting a Huber needle percutaneously into the silicone septum 28 of the injection port 18.

As is well known in the field the adjustable gastric band 10 may be made from any suitable medically compatible material having sufficient strength necessary for a particular laparoscopic surgery or particular patient.

As mentioned above, the two ends of the adjustable gastric band 10 are attached together (the specific attachment mechanism structure is not illustrated in FIG. 1). The present invention is directed to various embodiments of opposing surface attachment mechanisms for connecting the two ends together. The general construction of adjustable gastric band 10 shown in FIGS. 1 and 2 and described above is common to the embodiments illustrated in FIGS. 3-10, with the embodiments differing by the specific attachment mechanisms. It is noted that the practice of the present invention may be used with any band, and is not limited to use with an adjustable gastric band having the exact features described above or below.

Figure 3:
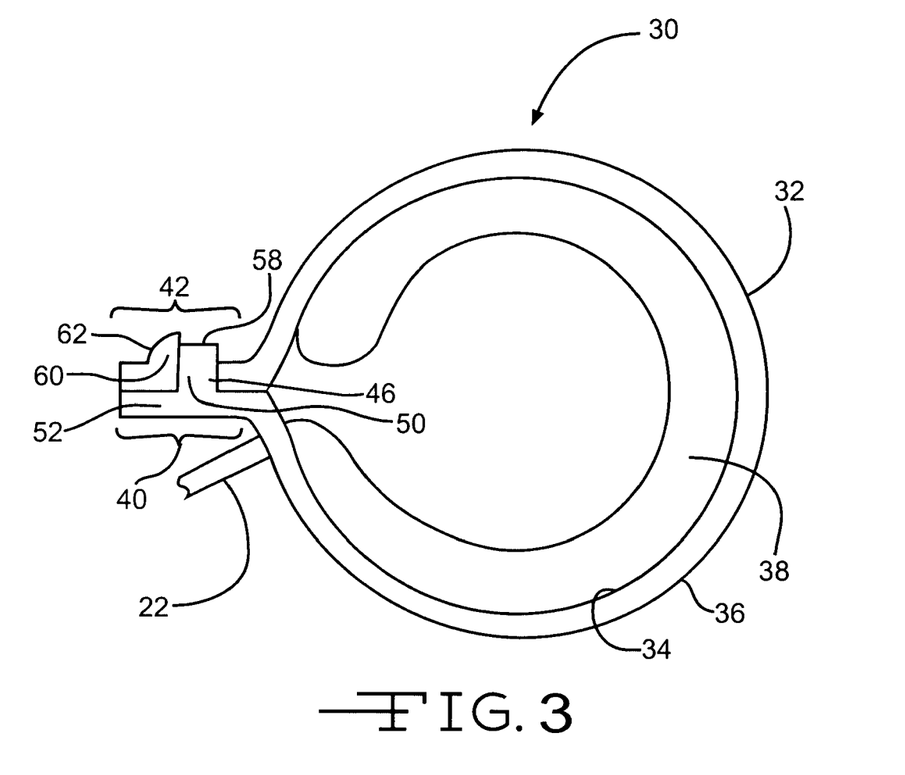
FIG. 3 is a top view of an adjustable gastric band constructed in accordance with the present invention having an opposing inner surface attachment mechanism.

Turning now to FIG. 3, the adjustable gastric band 30 includes an elongated strap 32 extending in what is referred to herein as the longitudinal direction, even though when implanted the adjustable gastric band 30 has an arcuate configuration. The strap 32 includes an inner surface 34 and an outer surface 36, with the balloon 38 extending inwardly from adjacent the inner surface 34. The adjustable gastric band 30 includes a first end portion 40 which abuts a second end portion 42, with the inner surface 34 of the adjustable gastric band 30 at the first end portion 40 being disposed adjacent the inner surface 34 of the adjustable gastric band 30 at the second end 42 portion.

Figure 4:
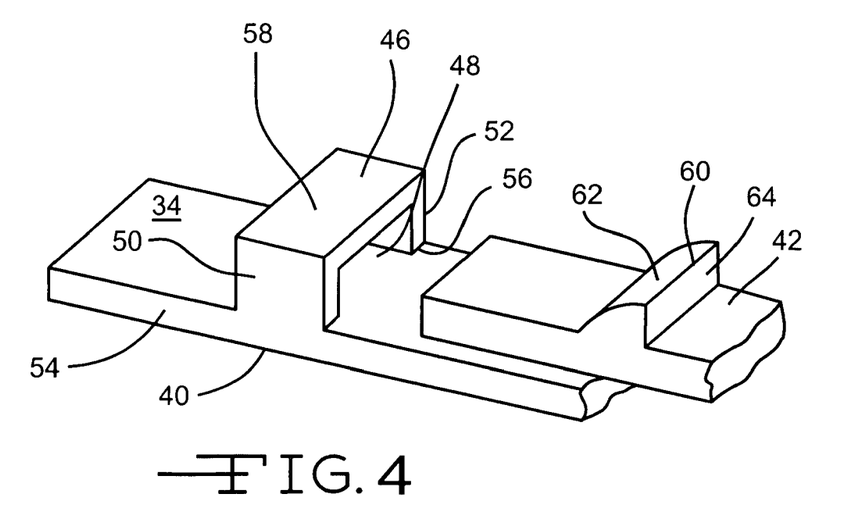
FIG. 4 is an enlarged, fragmentary perspective view of the opposing inner surface attachment mechanism of the adjustable gastric band of FIG. 3.

Referring also to FIG. 4, which illustrates the opposing inner surface attachment mechanism of the adjustable gastric band of FIG. 3, the first end portion 40 includes a laterally extending member 46 which extends generally perpendicularly from the inner surface 34. The member 46 is configured to engage the second end portion 42. More specifically, the laterally extending member 46 defines a passageway 48 in conjunction with the inner surface 34 at the first end portion 40 which is configured to receive the second end portion 42. The member 46 includes two spaced apart legs 50, 52 which extend from the inner surface 34 at the opposite edges 54, 56 of the strap 32, with a cross member 58 extending therebetween.

The second end 42 includes a retaining member 60 extending from the outer surface 36 thereof. The retaining member 60 includes an inclined surface 62 which may be arcuate as shown, or planar. The retaining member 60 also includes the retention surface 64 which extends generally perpendicular from the outer surface 36, and perpendicular to any relative movement between the first and second end portions 40, 42. The retention surface 64 must extend above the upper edge of the passageway 48 a distance sufficient to provide the desired force to resist disengagement. In the embodiment depicted, the retention surface 64 extends beyond the top of the cross member 58.

Figure 5A:
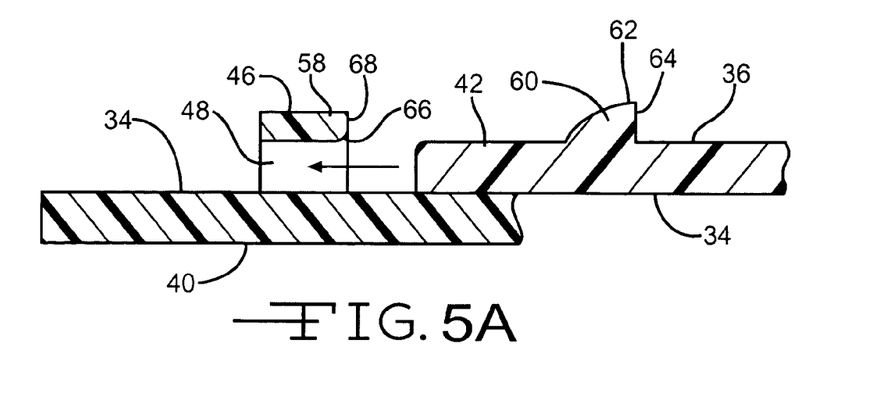
FIGS. 5A-C are s series of enlarged, fragmentary cross section side views of various stages of engagement of the ends of the opposing inner surface attachment mechanism shown in FIG. 3, taken along the longitudinal midline of the adjustable gastric band.
Figure 5B:
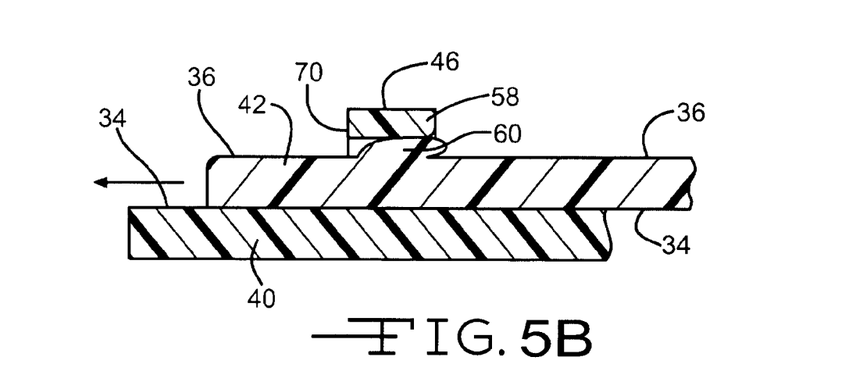
Figure 5C:
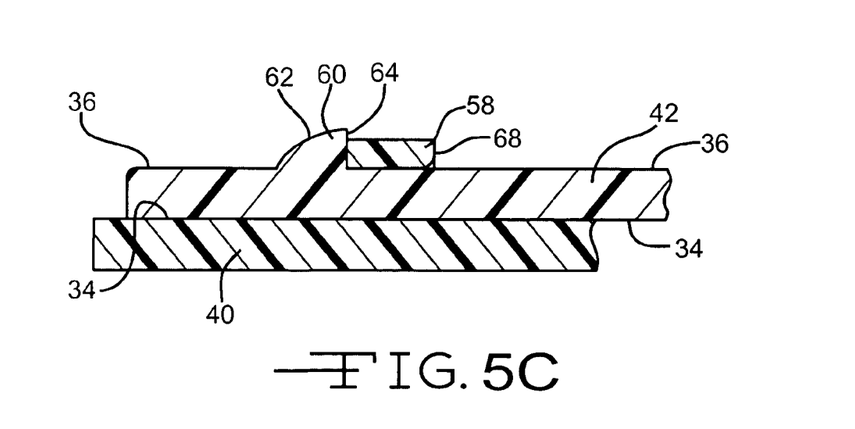

Referring now to FIGS. 5A-C, there are shown a series of enlarged, fragmentary cross section side views of various stages of engagement of the first and second ends 40, 42. FIG. 5A, similar to FIG. 4, illustrates first and second end portions 40, 42 abutting each other, with the respective inner surface 34 of each disposed adjacent, and in contact with each other.

In FIG. 5B, the second end portion 42 has been advanced toward engagement with the second end portion 42 being received by the laterally extending member 46, with the retaining member 60 disposed within passageway 48. As shown, the retaining member 60 is compressed and the height of passageway 48 has expanded by stretching of the laterally extending member 46 sufficiently to permit the second end portion 42 and the retaining member 60 to be inserted through passageway 48. The laterally extending member 46, the retaining member 60 and the laterally extending member 46 are sufficiently resilient to permit this interaction. The cross member 58 includes a lead-in surface 66 to assist the insertion of second end portion 42 into passageway 48 and the passage of retaining member 60.

FIG. 5C illustrates laterally extending member 46 in engagement with the second end portion 42, with the retention surface 64 of the retaining member 60 adjacent the surface 70 so as to resist undesired withdrawal of the second end portion 42 which would disengage the second end portion 42 from the first end portion 40. The force required to disengage the two end portions 40, 42, is low enough to be overcome when it is desired to remove the adjustable gastric band.

Figure 6:
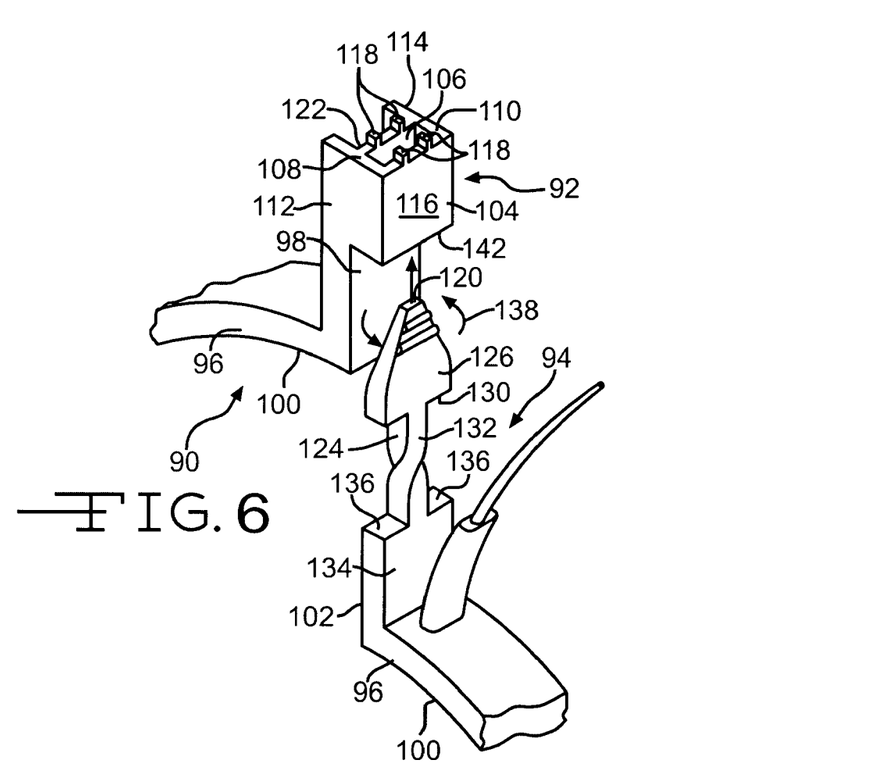
FIG. 6 is an enlarged, fragmentary perspective view of another embodiment of an adjustable gastric band having an opposing inner surface attachment mechanism.
Figure 7:
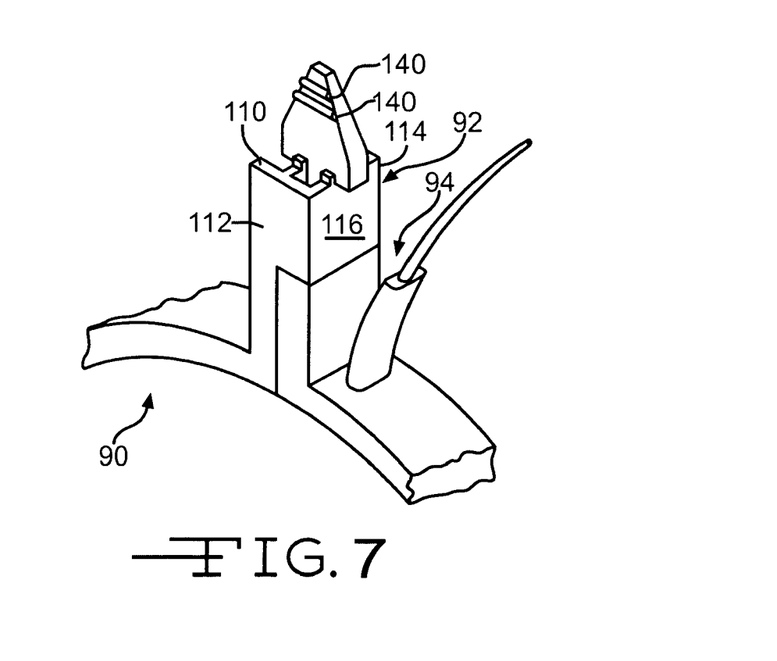
FIG. 7 is an enlarged, fragmentary perspective view of the opposing inner surface attachment mechanism of the adjustable gastric band shown in FIG. 6, in the engaged position.

FIGS. 6 and 7 show another embodiment of an adjustable gastric band 90 having another configuration of an opposing inner surface attachment mechanism. The first end portion 92 abuts the second end portion 94. Although the first end portion 92 is illustrated as forming a 90° angle with the strap 96, in regard to this embodiment the surface 98 of the first end portion 92 is considered a continuation of the inner surface 102. Similarly, the surface 102 of the second end portion 94 is a continuation of the inner surface 100.

The first end portion 92 includes a laterally extending member 104 which extends generally perpendicularly from the surface 98. The member 104 is configured to engage the second end portion 94. The laterally extending member 104 defines a passageway 106 in conjunction with the surface 98 at the first end portion 92 which is configured to receive the second end portion 94. The member 104 includes two spaced apart legs 108, 110 which extend from the surface 98 at the opposite edges 112, 114, with a cross member 116 extending therebetween. A plurality of spaced apart protrusions 118 extend from the distal end 120 of first end portion 92. A relief 122 is formed at the outside of first end portion 92 due to molding considerations.

The second end 94 includes a retaining member 124, having an arrowhead shaped distal end 126. As seen in FIGS. 6 and 7, the arrowhead has a narrow tip 128 and a wide base 130. The distal end 126 is disposed at the end of an elastic shaft 132 which extends generally perpendicularly from a base portion 134 of second end portion 94, with transverse surfaces 136.

To engage the two end portions 92, 94 together, the distal end 126 is rotated as indicated by the arrows 138 so that the base 130 of the arrowhead is generally aligned with the passageway 106. Since dimensions of distal end 126 are complementary to the dimensions of passageway 106, distal end 126 may easily pass therethrough. The distal end 126 is inserted through the passageway 106, and is pulled out such that the base 130 is completely past the distal end 120, elongating the shaft 132. Ribs 140 allow for easier gripping of distal end 126.

Once pulled through the passageway 106, the distal end 126 is rotated back to its normal orientation, extending in the longitudinal direction not in alignment with the passageway 106. The base 130 is located between the protrusions 118, with the elastic shaft 132 urging the base 130 against the distal end 120. Thus, the distal end 126 tends to remain in its normal orientation as shown in FIG. 7.

Figure 8:
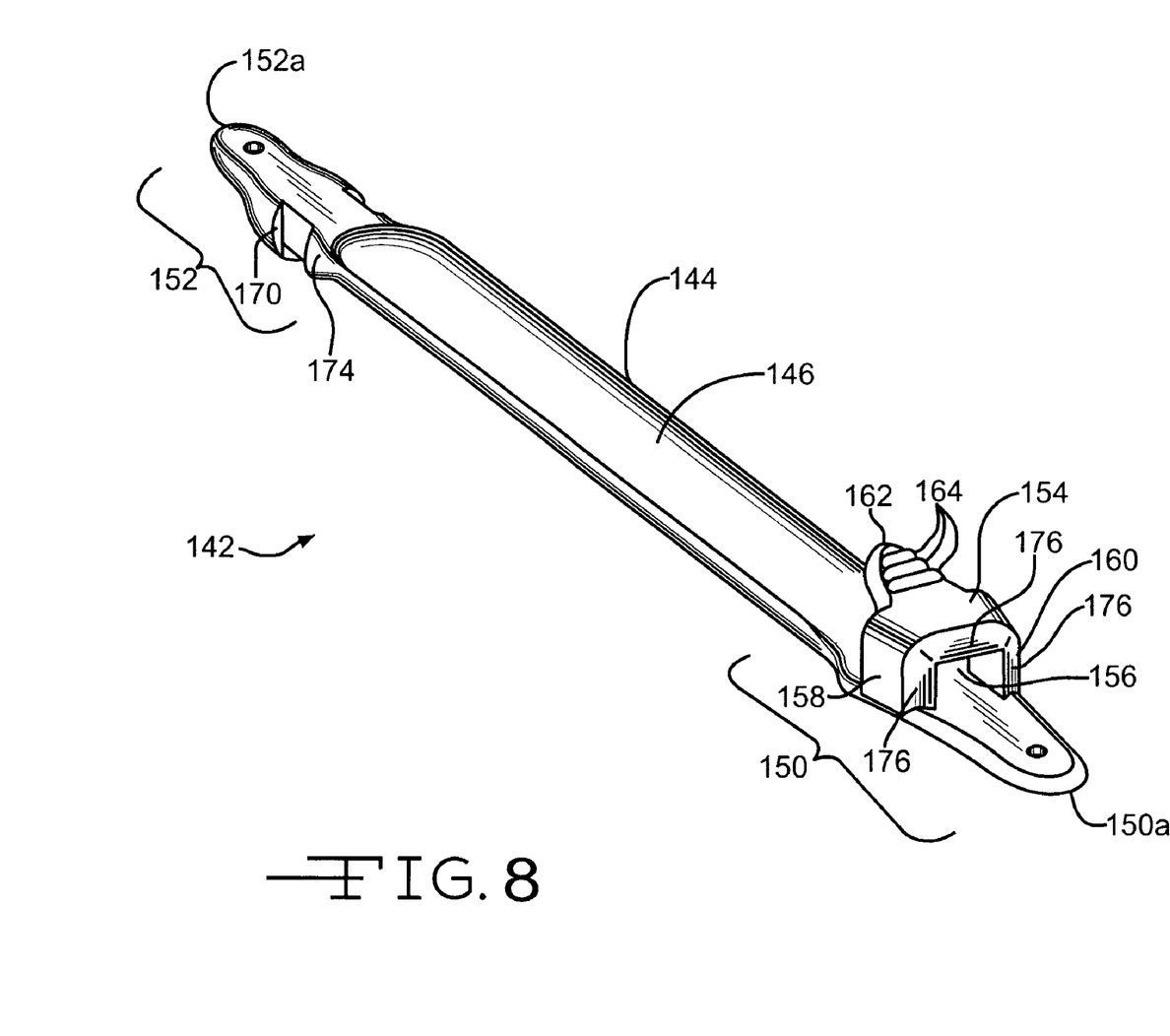
FIGS. 8 and 9 are perspective views of another embodiment of an opposing inner surface attachment mechanism in accordance with the present invention.
Figure 9:
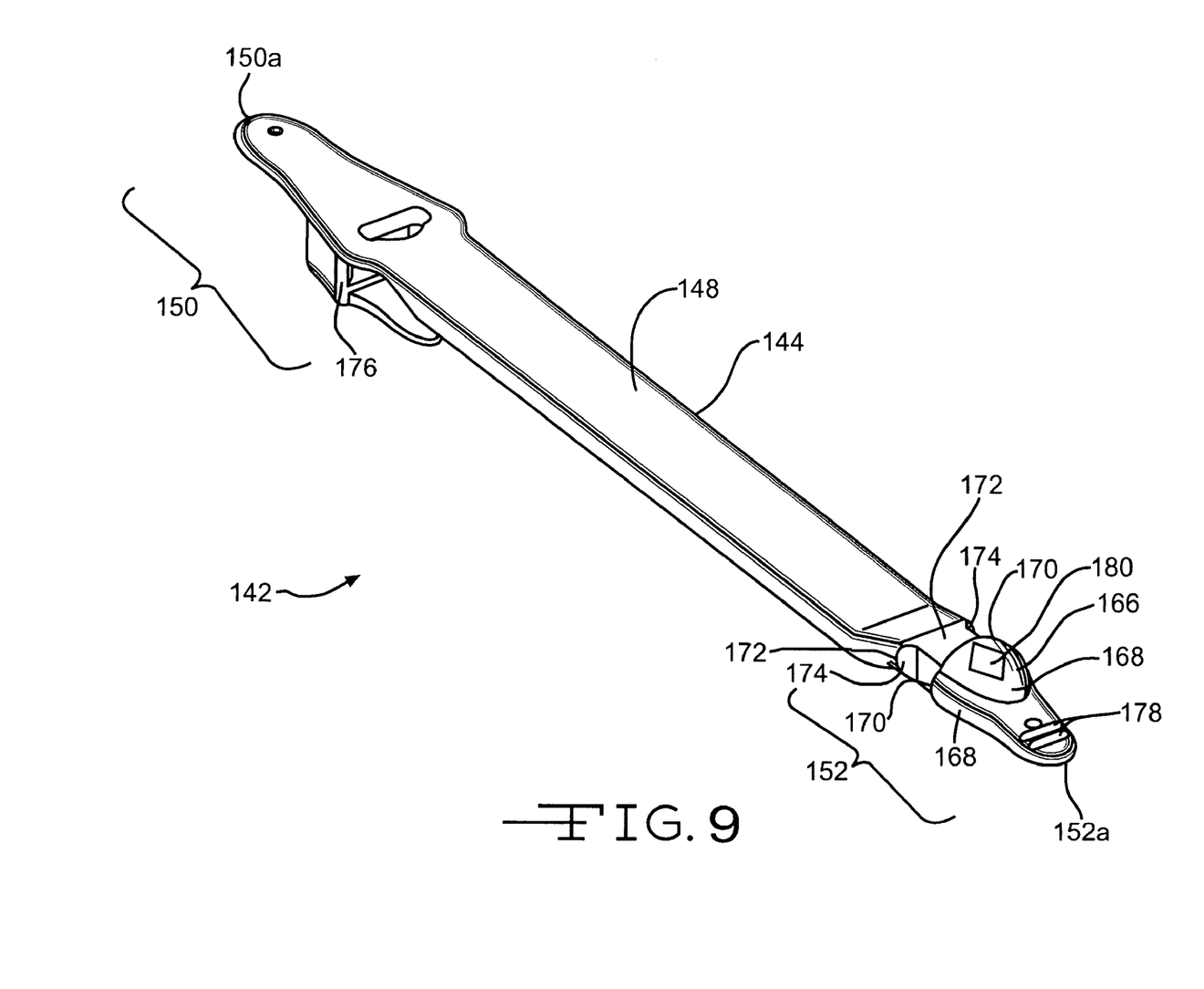

FIGS. 8 and 9 illustrate another embodiment of an opposing inner surface attachment mechanism. The adjustable gastric band 142 includes an elongated strap 144 which includes an inner surface 146 and an outer surface 148. The band 142 includes a first end portion 150 and a second end portion 152. When the band 142 is implanted around the stomach, the inner surface 146 of the first end portion 150 abuts the inner surface 146 of the second end portion.

The inner surfaces 146 are attached to each other by means of the opposing inner surface attachment mechanism. The first end portion 150 includes a laterally extending member 154, extending generally perpendicularly from the inner surface 146, which is configured to engage the second end portion 152. The laterally extending member 154 defines a passageway 156, and includes two spaced apart upright legs 158 and 160, with a cross member 162 extending therebetween.

The member 154 includes a tab 162 extending from the cross member 154, away from the distal end 150a of the first end portion. The tab 162 includes a plurality of ribs 164, which provide a better grip to grab the tab 162 to provide the opposing force then pulling the distal end 152a of the second end portion 152 through the passageway 156.

The second end portion 152 includes a retaining member 166 extending from the outer surface 148. The retaining member 166 includes an inclined leading surface 168 at the top and sides, to allow the retaining member 166 to pass relatively easily through the passageway 156 when attaching the two ends together. The retaining member 166 includes the retention surfaces 170 extending outwardly therefrom.

The second end portion 152 includes a neck portion 172 adjacent the retaining member 166. The base 172 of the neck portion 170 includes angled surfaces 174 which engage, when connected together, complementarily shaped and oriented surfaces 176 at the corresponding side of the member 154. The angled surfaces 174 lead from the base 172 to the reduced transverse width of the neck portion 172. The height and width of the neck portion corresponds to the dimensions of the passageway 156, and may be offset from the rest of the strap 144.

The retaining surfaces 170 extend from the retaining member 166 at the location where the neck portion 172 joins the retaining member 166. The retaining surfaces 170 extend beyond the sides of the passageway 156 to engage the corresponding surfaces 176 of the lateral member 154. The retaining surfaces 170 may be, as shown, inclined away from the distal end 152a, with the surfaces 176 being complementary thereto.

The distal end 152a is tapered extending forward of the retention member 166, and includes a plurality of ribs 178 which enhance gripping the distal end 152a. A surface configuration 180, shown as a recessed diamond shape, may be included as a visual indicator of the proper placement of the retention member 166 when the two ends are attached, extending beyond the passageway 156, so that the surfaces 170 and 176 abut each other.

The ability to withdraw the second end portion 152 through the passageway 156 to separate it from the first end portion 150 may be assisted by the inclusion of a relief or cavity formed in the retention member 166. For example, a circular or diamond shaped laterally extending cavity may be formed at or near the surface configuration 180, without affecting the retention of the second end portion 152. Upon squeezing the retaining member 166 adjacent such a relief or cavity, the resilience would allow transverse compression of the retaining member 166, to be more easily withdrawn back through the passageway 156. A resilient element, functioning as a spring, could also be molded in place adjacent such a cavity.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

Thus, as used herein and in the claims, an implantable band is a band which may be implanted in a position to occlude flow, such as food or body fluids, through an anatomical passageway, such as a stomach or lumen.

In summary, numerous benefits have been described which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The one or more embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An implantable band for treatment of a medical condition, the band, comprising:
    (a) a strap configured to encircle a portion of an anatomical passageway, said strap having an inner and outer surface;
    (b) said strap including first and second end portions disposed at either end of said strap, said first and second end portions including respective inner and outer surfaces which correspond to said inner and outer surfaces of said strap, said first end portion having a first distal end, said second end portion having a second distal end;
    (c) a laterally extending member extending laterally from said inner surface of said first end, said laterally extending member defining a passageway, said laterally extending member having a first leading edge proximal said first distal end and a first trailing edge;
    (d) said second end portion comprising a retaining member having a generally tapered shape terminating in a second trailing edge so as to be easily passed through said passageway to an attached position, said second trailing edge comprising at least one retention surface extending therefrom and positioned to engage said first leading edge when said second end portion is disposed in said attached position, said at least one retention surface cooperating with said first leading edge to resist withdrawal of said retaining member from said passageway;
    wherein said second end portion includes a neck portion adjacent said retaining member, said neck portion having a reduced cross section relative to the band and retaining member adjacent the neck portion, said neck portion including a base configured to cooperate with said first trailing edge to resist said base portion being pulled through said passageway;
    wherein said neck portion is sized such that the neck portion is under tension when said second end portion is disposed in said attached position.

2. The band of claim 1, wherein said at least one retention surface is inclined outwardly away from said second distal end, and said first leading edge is inclined complementarily to said at least one retention surface.

3. The band of claim 1, wherein said neck portion includes at least one angled surface which engages a complementarily shaped angled surface of said first trailing edge.

4. The band of claim 1, wherein said retaining member comprises a resilient element.

5. The band of claim 1, wherein said retaining member comprises a cavity.

6. The band of claim 1, wherein said laterally extending member comprises a tab extending therefrom.

7. The band of claim 1, wherein said second trailing edge has a normal orientation such that said retaining member must be rotated from said normal orientation to align said retaining member with said passageway prior to disposing said retaining member through said passageway.

8. The band of claim 7, wherein the first leading edge of the laterally extending member comprises at least one pair of spaced apart members extending therefrom, wherein said spaced apart members define a gap therebetween which is configured to receive said second trailing edge in said normal orientation.

9. The band of claim 1, wherein said retaining member has an arrowhead shape.

10. An implantable band for treatment of a medical condition, the band comprising:
    (a) a strap configured to encircle a portion of an anatomical passageway, said strap having an inner and outer surface;
    (b) said strap including first and second end portions disposed at either end of said strap, said first and second end portions including respective inner and outer surfaces which correspond to said inner and outer surfaces of said strap, said first end portion having a first distal end, said second end portion having a second distal end;
    (c) a laterally extending member extending laterally from said inner surface of said first end, said laterally extending member defining a passageway, said laterally extending member having a first leading edge proximal said first distal end and a first trailing edge;
    (d) said second end portion comprising a retaining member having a generally tapered shape terminating in a second trailing edge so as to be easily passed through said passageway to an attached position, said second trailing edge comprising at least one retention surface extending therefrom and positioned to engage said first leading edge when said second end portion is disposed in said attached position, said at least one retention surface cooperating with said first leading edge to resist withdrawal of said retaining member from said passageway;
    wherein said second end portion includes a neck portion adjacent said retaining member, said neck portion having a reduced cross section relative to the band and retaining member adjacent the neck portion, said neck portion including a base configured to cooperate with said first trailing edge to resist said base portion being pulled through said passageway;
    wherein said neck portion includes at least one angled surface which engages a complementarily shaped angled surface of said first trailing edge.

11. The band of claim 10, wherein said at least one retention surface is inclined outwardly away from said second distal end, and said first leading edge is inclined complementarily to said at least one retention surface.

12. The band of claim 10, wherein said neck portion is sized such that the neck portion is under tension when said second end portion is disposed in said attached position.

13. The band of claim 10, wherein said retaining member comprises a resilient element.

14. The band of claim 10, wherein said retaining member comprises a cavity.

15. The band of claim 10, wherein said laterally extending member comprises a tab extending therefrom.

16. The band of claim 10, wherein said second trailing edge has a normal orientation such that said retaining member must be rotated from said normal orientation to align said retaining member with said passageway prior to disposing said retaining member through said passageway.

17. The band of claim 16, wherein the first leading edge of the laterally extending member comprises at least one pair of spaced apart members extending therefrom, wherein said spaced apart members define a gap therebetween which is configured to receive said second trailing edge in said normal orientation.

18. The band of claim 10, wherein said retaining member has an arrowhead shape.

\* \* \* \* \*